US010226398B2

United States Patent
Tseng

(10) Patent No.: US 10,226,398 B2
(45) Date of Patent: Mar. 12, 2019

(54) OPTICAL NEEDLE WITH LIGHTGUIDE GROOVE

(71) Applicant: Hsiao-Sen Tseng, Taichung (TW)

(72) Inventor: Hsiao-Sen Tseng, Taichung (TW)

(*) Notice: Subject to any disclaimer, the term of this patent is extended or adjusted under 35 U.S.C. 154(b) by 456 days.

(21) Appl. No.: 15/010,993

(22) Filed: Jan. 29, 2016

(65) Prior Publication Data

US 2017/0087055 A1  Mar. 30, 2017

(30) Foreign Application Priority Data

Sep. 24, 2015 (TW) .............................. 104131667 A

(51) Int. Cl.
| | |
|---|---|
| *A61H 39/08* | (2006.01) |
| *F21V 8/00* | (2006.01) |
| *A61N 5/06* | (2006.01) |
| A61H 39/00 | (2006.01) |
| A61N 5/067 | (2006.01) |

(52) U.S. Cl.
CPC ......... *A61H 39/086* (2013.01); *A61N 5/0619* (2013.01); *G02B 6/0005* (2013.01); *A61H 2039/005* (2013.01); *A61H 2201/0188* (2013.01); *A61H 2201/10* (2013.01); *A61N 2005/063* (2013.01); *A61N 2005/067* (2013.01)

(58) Field of Classification Search
CPC ............ A61H 39/086; A61H 2039/005; A61H 2201/0188; A61H 2201/10; A61N 5/0619; A61N 2005/063; G02B 6/0005; A61B 18/22
USPC ....................................................... 606/189
See application file for complete search history.

(56) References Cited

U.S. PATENT DOCUMENTS

| | | | | |
|---|---|---|---|---|
| 3,943,932 A | * | 3/1976 | Woo ....................... | A61H 39/08 128/907 |
| 4,729,621 A | * | 3/1988 | Edelman .............. | G02B 6/4203 385/33 |
| 2002/0173831 A1 | * | 11/2002 | Costa Dos Santos ...................... | A61H 39/08 607/88 |
| 2012/0123398 A1 | * | 5/2012 | Hiereth .................. | A61B 18/22 606/16 |
| 2014/0121538 A1 | | 5/2014 | Hendriks et al. | |
| 2014/0243806 A1 | | 8/2014 | Srinivasan | |

(Continued)

FOREIGN PATENT DOCUMENTS

| | | |
|---|---|---|
| CN | 103901233 A | 7/2014 |
| CN | 104287960 A | 1/2015 |
| CN | 204073134 U | 1/2015 |

(Continued)

*Primary Examiner* — Tuan V Nguyen
(74) *Attorney, Agent, or Firm* — Muncy, Geissler, Olds & Lowe, P.C.

(57) ABSTRACT

Disclosed is an optical needle comprising a coupling seat, a needle body in connection with the coupling seat and at least an optical fiber. The needle body comprises a lightguide groove extended along the length direction of the needle body to accommodate a portion of the optical fiber. The coupling seat provides a junction plane to couple a light source. An end of the lightguide groove is aligned with the junction plane, so to align an end of the optical fiber with the junction plane. The optical needle is characterized in that the long axis of the optical fiber reduces from a section aligned with the junction plane to an end adjacent to the needle body. A method for preparation of the optical needle is also disclosed.

16 Claims, 5 Drawing Sheets

(56) References Cited

U.S. PATENT DOCUMENTS

2015/0057530 A1* 2/2015 Roggeveen .......... A61B 5/0053
600/424

FOREIGN PATENT DOCUMENTS

| TW | M493360 U | 1/2015 |
|---|---|---|
| WO | WO2014133500 A1 | 9/2014 |

* cited by examiner

OPTICAL NEEDLE WITH LIGHTGUIDE GROOVE

TECHNICAL FIELD OF THE INVENTION

The present invention relates to an optical needle, in particular to a puncture needle having a lightguide groove, for the transmission of a light beam into an object.

PRIOR ART

The puncture needle is a tool widely used in industry, services and daily life. In many applications, a puncture needle needs to have a light-guiding function. Such applications include industrial detection, medical detection and treatment.

Recently, stimulations by puncture needles at certain "acupoints" of the human body, in order to improve the physical conditions of a person have become a popular application in many countries. One of such applications is called "acupuncture", where a puncture needle is inserted into the human body through the skin, to reach the position of an acupoint, and thermal, optical or electrical energy is applied to the acupoint through the puncture needle, in order to stimulate physiological reactions at the acupoint. One way to apply the energy is to burn the external portion of the puncture needle, in order to transmit the thermal energy to the acupoint through the puncture needle. Another way is to apply an electricity to the needle, in order to transmit the electrical energy to the acupoint through the needle. A most recent application of the puncture needle is to apply a light beam, in particular a laser beam, to the acupoint through the puncture needle.

In order to transmit light beams through a puncture needle, many optical needles to be used in medical or acupuncture applications have been developed. In addition, optical needles for other applications based on transmission of light beams through a puncture needle, such as detections using the light beams so transmitted, have also been developed.

CN103901233A discloses a probe with an optical fiber. An end of the optical probe is etched to form a tip with an oval end surface. A metal coating is provided around the tip, with the tip exposed from the coating.

CN104287960A discloses an acupuncture needle with an optical fiber provided inside the acupuncture needle. An end of the optical fiber forms a tapered tip at a micro pore of the tip of the acupuncture needle, to guide a laser beam into a target position of the needle. Other micro pores are provided for the transmission of electrical and optical signals.

CN204073134 discloses a multi-channel laser treatment equipment, including eight mutually independent laser treatment channels, each including a laser light source and an optical fiber. Laser light is provided in the form of continuous or pulsed irradiations to irradiate an acupoint.

TW M493360U discloses an optical needle for intravenous irradiations. The optical needle provides a through hole at its base. An end of the through hole may be connected by a tube, to be inserted by an optical fiber, such that the optical fiber passes through the through hole. A cap is provided to seal the through hole, after the optical fiber is sterilized.

US 2014/0121538A1 discloses an assembly of an optical fiber and a metal needle, which provides a plurality of optical fiber tunnels therein. The tip of the needle forms two tilt angles so that an end of the optical fiber protruding from a second tilt angle, without protruding from the first tilt angle.

US 2014/0243806A1 discloses a hollow needle with optical fibers embedded therein. A plurality of tunnels is provided in the needle, to accommodate the plurality of optical fibers. A hub is provided to connect the plurality of optical fibers to a laser source. In the hub, a plurality of lightguides is provided, to guide laser beams from the laser source to the respective optical fibers.

WO 2014/133500A1 discloses a diagnostic probe. The probe includes a needle body provided with a plurality of tunnels to accommodate optical fibers. The respective optical fibers terminate at different longitudinal positions of the needle body, to collect diagnostic information of tissues surrounding the terminals.

Observations in the development of the conventional optical needle reveal that certain puncture needles have been designed to provide a light-guiding function. These optical needles, however, used a complicated needle body structure. Most conventional optical needles use a needle tube to support optical fiber(s) in the tube for providing the required light-guiding function. The needle tube is made of metal or other rigid materials. Forming a hollow in the needle body and assembling an optical fiber in the hollow are both difficult and time consuming. In addition, the optical fiber would occupy the full hollow, therefore there is no space left for the transmission of other fluid, electricity or lights in the optical needle.

Nevertheless, most optical needles are connected to a separate light source through an optical fiber. In order to connect the lightguide embedded in the optical needle to the optical fiber that is capable of transmitting a light beam for a certain distance, a coupler to align the lightguide and the optical fiber will be necessary. The coupler makes the optical needle system bulky and adds additional costs to the manufacture and application of the system.

OBJECTIVES OF THE INVENTION

The objective of the present invention is to provide a novel structure for the optical needle, such that the lightguide material of the optical needle does not occupy the main channel of the optical needle.

Another objective of the present invention is to provide an optical needle that may be easily coupled to a light source without the need of an optical coupler.

Another objective of the present invention is to provide an optical needle that is easy to assemble.

Another objective of the invention is to provide a novel method for the preparation of an optical needle, wherein the lightguide material of the optical needle does not occupy the main channel of the optical needle.

SUMMARY OF THE INVENTION

According to this invention, an optical needle is provided and comprises a needle body and a light source coupling seat. The optical needle may optionally comprise a lightguide, such as an optical fiber. The needle body provides a lightguide groove to accommodate a portion of the lightguide. The light source coupling seat provides a junction plane for interfacing a light source and the lightguide. An end of the lightguide groove is aligned with the junction plane of the light source coupling seat, such that an end of the lightguide is aligned with the junction plane. A lightguide cavity is formed in the light source coupling seat to accommodate the lightguide. The lightguide cavity extends from an end adjacent to the junction plane to an end adjacent to the lightguide groove and a cross-sectional size of the cavity reduces from the junction plane end to the lightguide groove end. Reduction of the cavity size may be a continuous reduction or a gradient reduction.

If the optical needle includes the lightguide, the lightguide is accommodated in the lightguide cavity and extends from the junction plane end to the lightguide groove end of the lightguide cavity, then to the tip of the optical needle along the lightguide groove. In addition, the long axis of the cross section of the lightguide reduces from a section at the junction plane end of the lightguide cavity to a section at the lightguide groove end of the lightguide cavity. In the preferred embodiments of the invention, the long axis is diameter of the lightguide. The reduction of the long axis may be a continuous reduction or a gradient reduction. The junction plane may be provided in a recess, which may accommodate a light source.

In a particular application of the invention, the optical needle is used to transmit light beams into an object, such as a human tissue, a longitudinal tube or a pouch. The tip of the needle body may have a diagonal cut to facilitate puncture purposes of the needle. A top of the needle body may extend laterally to form a disc or a funnel-like infundibulum, to strengthen the integrity of the needle body and the light source coupling seat.

The optical needle of the present invention may connect a light source at the junction plane. The light source may be an optical fiber cable or a laser head. If the light source is a laser head, the laser head may comprise a laser beam generator for generating a laser beam; a power supply for providing power to the laser beam generator; a coupler to couple the light source to the coupling seat; and a switch for the control of the power supply. The laser head may provide a coupling portion with a protrusion having a shape complimentary to the shape of the recess of the light source coupling seat. The coupling portion may also have a recess with a shape complimentary to the shape of a protruding portion of the light source coupling seat. The protrusion and/or recess of the coupling portion facilitates stable insertion of the laser lead in the light source coupling seat and the alignment of the light emitting surface of the laser lead to the junction plane end of the lightguide.

The present invention also discloses a preparation method of optical needle. The method comprises: preparing a needle body with a lightguide groove; providing a lightguide with a first section, a narrowing section connected to the first section and a second section connected to the narrowing section. The long axis of the cross section of the lightguide reduces from a junction of the first and narrowing sections to a junction of the narrowing and second sections. The method further comprises: disposing the second section of the lightguide in the lightguide groove; if necessary, leaving the first and/or narrowing section outside of the lightguide groove; forming a light source coupling seat with a light source junction plan, such that the light source coupling seat encompasses a portion of the needle body and the first and narrowing sections of the lightguide and that a first end of the lightguide is aligned with the light source junction plane, to receive light beams entering through the light source junction plane. The junction plane may be provided in a recess, such that the first section of the lightguide is aligned with the recess, after the light source coupling seat is formed. The step of forming the light source coupling seat may further comprise a step of forming a recess in the light source coupling seat. The method may further include a step of sealing the lightguide groove.

In a preferred embodiment of this invention, the lightguide groove is provided substantially at the cross-sectional center of the needle body. In other preferred embodiments, the position of the lightguide groove deviates from the cross-sectional center of the needle body. In one particular example, the lightguide groove is provided in the wall of the needle body. The light source coupling seat may be formed by mold casting. The step of sealing the lightguide groove may comprise coating a surface of the needle body with a plastic material. Forming of the light source coupling seat and sealing the lightguide groove may be completed in one mold casting step.

These and other objectives and advantages of present invention maybe clearly appreciated from the detailed description by referring to the following drawings.

DETAILED DESCRIPTION OF THE INVENTION

The present invention provides a novel structure of optical needles and its preparation method. Although it is not intended to limit the present invention by any theory, the inventor has found that one reason that makes the conventional optical needles complicated in structure is size of lightguide or optical fiber used in the optical needle; the size of lightguide is too small to be installed in the optical needle easily and is not compatible with that of the optical fiber/optical fiber cable used to transmit light beams from a light source at a relatively long distance. To connect the lightguide and the optical fiber/cable with high efficiency, a coupler is needed. The inventor also found that providing a lightguide groove in the optical needle may easily solve the technical problems in the conventional art. In addition, by reducing the long axis or diameter of a lightguide or an optical fiber along the longitudinal direction, the lightguide or optical fiber so obtained would be able to support the coupling of the lightguide/optical fiber with a light source or a laser source. An invention with these and other features is thus realized.

In the followings, the optical needle of the present invention will be described by using its several embodiments. It shall be appreciated that description of the embodiments serves merely to illustrate the basic structure and spirit of the present invention. They shall not be used to limit the scope of protection of this invention.

Figure 1:
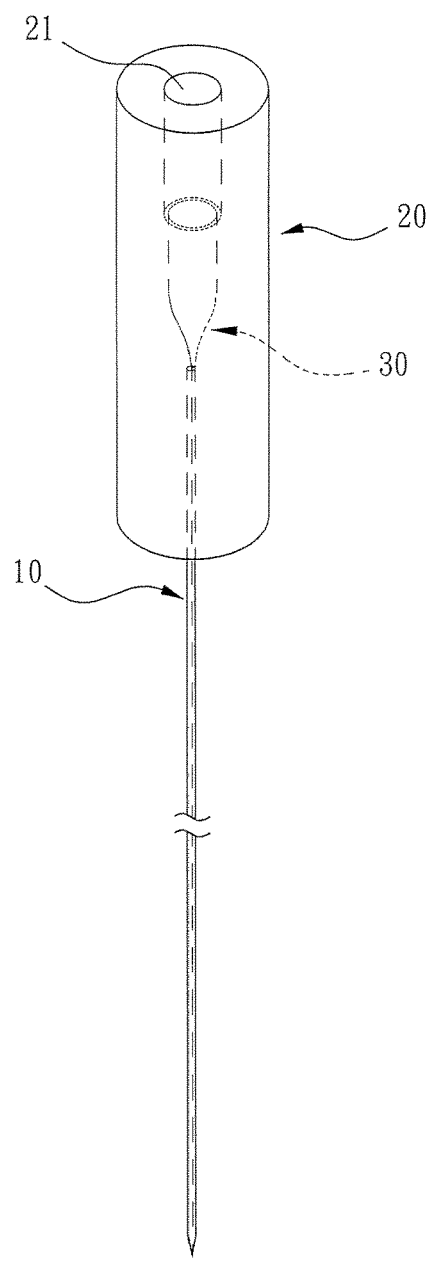
FIG. 1 shows the perspective view of one embodiment of the optical needle with lightguide groove of the present invention.
Figure 2:
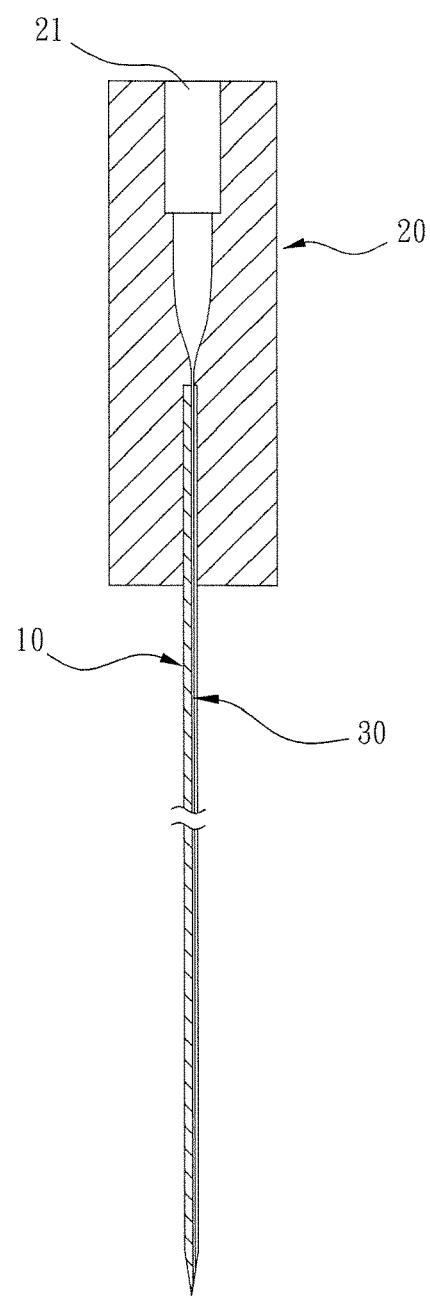
FIG. 2 shows the cross-sectional schematic view of the optical needle of FIG. 1.
Figure 3:
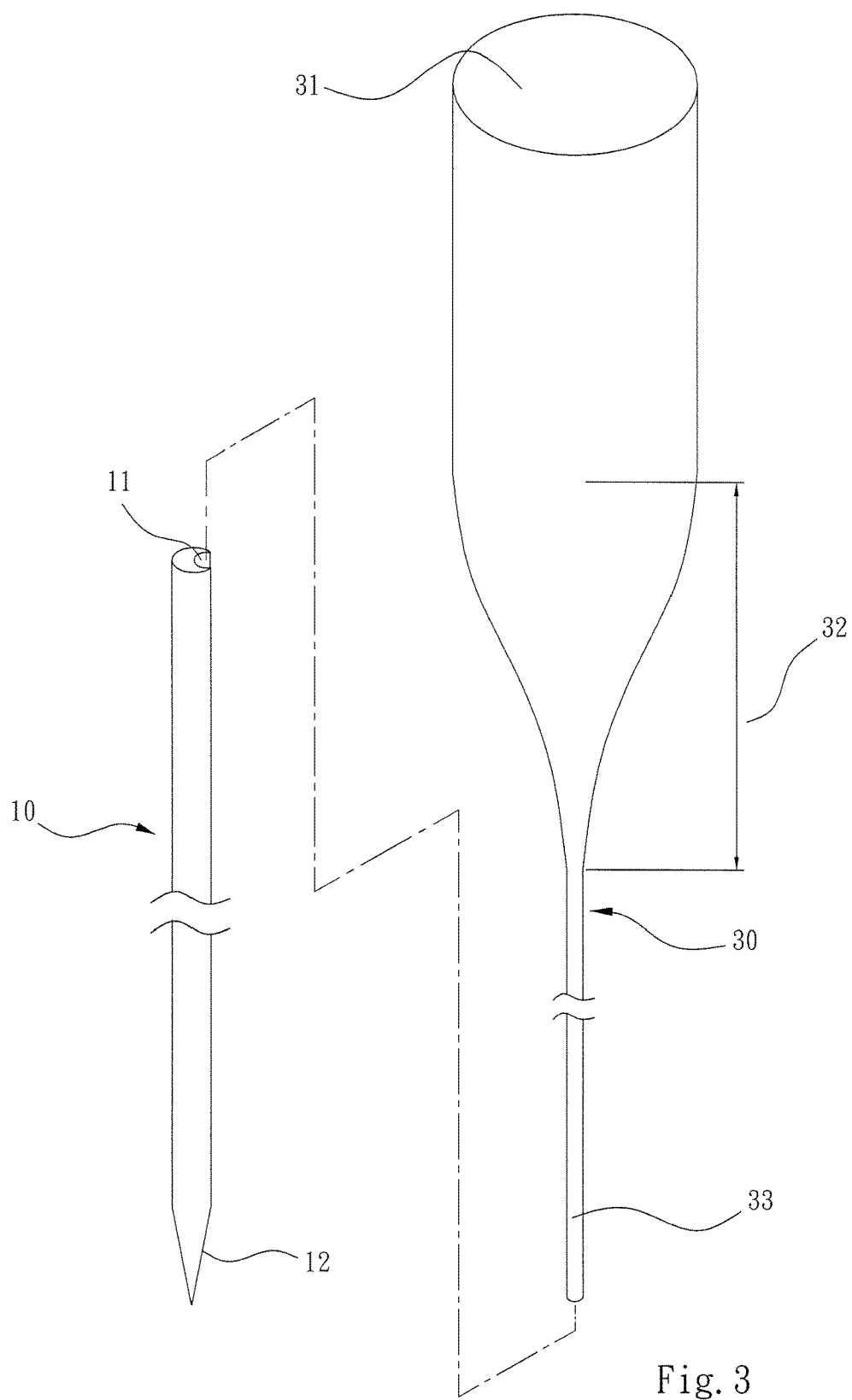
FIG. 3 is a schematic diagram of the optical needle of FIG. 1, after assembly.

FIG. 1 shows the perspective view of one embodiment of the optical needle with lightguide groove of the present invention and FIG. 2 shows its cross-sectional view. As shown, the optical needle of the present invention includes a needle body 10, a light source coupling seat 20 and a lightguide 30. The needle body 10 is provided with a lightguide groove 11 for receiving the second section 33 of the lightguide 30, in this case an optical fiber. FIG. 3 shows the embodiment after assembly.

In the preferred embodiment of the inventions, the needle body 10 may be made from any rigid material. Suitable materials include metal, plastics, glass, or carbon fiber. Although not shown in FIGS. 1 and 2, the top surface of the needle body 10 may extend in the lateral direction and forms a disc. The purpose of the disc shape is to strengthen the combination of the needle body 10 and the coupling seat 20. The inner diameter of the lightguide groove 11 of the needle body 10 shall be sufficient to accommodate a portion of the lightguide 30. For example, the inner diameter of the lightguide groove 11 is preferably not greater than the radius of the needle body 10 and shall not interfere with the punctuation function of the needle body 10. For these purposes, the inner diameter of the lightguide groove 11 is preferably equal to one quarter to one time the radius of the needle body 10.

In a preferred embodiment of the present invention, the tip of the needle body 10 may have a diagonal cut 12, to facilitate puncture function of the needle 10. The shape of the cut is not limited but is preferably a shape easy to produce.

The light source coupling seat 20 may be made from a rigid or flexible material. Suitable materials include plastic, silicone, resin and other plastic material. It is also possible to use metal, ceramic and other materials that are easy to process, to prepare the light source coupling seat 20. In the example of FIGS. 1 and 2, the top surface of the light source coupling seat 20 forms a plane. This, however, is not any technical limitation. For example, the top surface of the coupling seat 20 may be convex, concave or in another shape. The top surface may form a particular pattern or design, by using any applicable technique. It is also possible to form level difference, guide grooves or chamfer at the top of the needle body 10. The optical needle shown in FIGS. 1 and 2 is suited for acupuncture or heating.

In the example of FIG. 1, the light source coupling seat 20 provides a recess 21, which is open to the top surface of the coupling seat 20, whereby a cavity to accommodate a light source 40 is formed. The bottom of the recess forms a junction plane. Shape of the opening of the recess 21 preferably complements a contour of the corresponding portion of a light source (not shown), so that the light source can be securely received within the recess 21. For example, if the light source is an optical cable with a diameter of about 500 um, the recess 21 may provide an inner diameter of about 500 um, to be plugged by the optical cable. If the light source is a laser head, the laser head may provide a protrude with a diameter of about 500 um. In such a case, the recess 21 also provide an inner diameter of about 500 um for coupling of the laser head. The junction plane is preferably a plane. If no recess is provided in the light source coupling seat 20, the junction plane may be provided at a top surface of the coupling seat 20. A conventional mating sleeve or an adaptor or interconnector may also be used to strengthen the connection of the light source coupling seat 20 and the laser head, in place of or in addition to the recess and/or extrusion.

Those having ordinary skills in the art may appreciate that the junction plane provided in the light source coupling seat 20 is not necessarily a physical plane at the surface of an object. The junction plane may be an imaginary plane. Moreover, the junction plane may also be a top surface of the first section 31 of the lightguide 30.

The lightguide 30 may be any light guiding material and is preferably an optical fiber. Suitable materials for the lightguide 30 include: glass, plastic, metal oxides and the like. A protective film may be provided on the surface of the lightguide 30 by, for example, coating. There is no particularly limitation in the material of the protective film. The cross-sectional shape of the lightguide 30 may be elliptical, but may also be circular, square, or polygonal or in a figure-8 configuration. If necessary, the lightguide 30 can also be a beam of two or more optical fibers twisted together. In the following description, the lightguide will be described, taking the optical fiber as an example.

One of the features of the present invention is that the long axis of the lightguide 30 reduces from its light source section (first section) 31 to its needle body section (second section) 33. When an optical fiber of circular cross-section is used, the long axis is the diameter of the optical fiber. Reduction of the long axis may be a continuous reduction or a gradient reduction. Under this design, the lightguide 30 will include along its length direction: a first section 31, a narrowing section 32 connected to the first section 31, and a second section 33 connected to the narrowing section 32. The first section 31 is aligned with the junction plane of the coupling seat 20, to be coupled to the light source 40. The second section 33 is to be disposed within the hollow cavity 11 of the needle body 10, and to extend to the tip portion 12 of the needle body 10. The long axis, or diameter, of the lightguide 30 starts to reduce from the junction of the first section 31 and the narrowing section 32 and the reduction ends at the junction of the narrowing section 32 and the second section 33. In the application of the present invention, the long axis or diameter of the first section 31 may be between 200 um to 1000 um, preferably between 450 um to 500 um. The exact size of the first section 31 is not any technical limitation and is preferably compatible with the size of a light emitting surface of the light source 40. The long axis or diameter of the second section 33 may be between 30 um to 100 um, preferably between 40 um to 50 um. The exact size of the second section 33 is not any technical limitation and is preferably compatible with the size of a diameter of the tip portion 12. If the diameter of the needle body 10 at the tip portion is 100 um, the long axis or diameter of the second section 33 may be 40-50 um, so that the lightguide 30 may be easily disposed in the lightguide groove 11 of the needle body 10.

The second section 33 preferably terminates at the needle tip 12, while it may retract within the needle tip or extend beyond the needle tip. The light guide may be a side light optical fiber or tail light optical fiber, depending on the purpose of use.

Method for forming the narrowing section 32 of the lightguide 30 is not limited but is preferably a technique to produce a gradual or progressive reduction in the long axis of an elongated lightguide, such as an optical fiber. Suitable methods include heating stretch at high temperature, molding and other methods. Among them, stretching at high temperature produces an optical fiber with continuously reduced long axis; the product is advantageous in transmission of light beams. Molding method forms a lightguide with gradient reduction in long axis, the advantage of which is accuracy in size of each section. Length of the narrowing section 32 is not particularly limited, but is preferably as short as possible. For example, if the long axis of the first section 31 is 500 um in length and the long axis of the second section 33 is 50 um in length, length of the narrowing section 32 can be 1 mm to 5 mm, so that the reduction ratio is 1/10 to 1/2 per mm. This ratio can reduce the length of the narrowing section 32, while efficient transmission of optical power is obtained. Other reduction ratios can also be used in the present invention, to obtain the same or similar effects. In addition, the reduction ratio is not necessarily linear.

The lightguide groove 11 of the needle body 10 is provided to accommodate a lightguide 30. In one preferred embodiment of this invention, the lightguide groove 11 is provided at the cross-sectional center of the needle body 10 and extends along the longitudinal direction of the needle body 10. In other embodiments, the needle body 10 has a tube-shape and the lightguide groove 11 is provided in the wall of the tube, extended along the longitudinal direction of the needle body 10. In the latter examples, the optical needle may be used to transport other fluid or to accommodate a medium for electricity or signal transmission. Method for forming the lightguide groove 11 is not limited. Any known art may be used to prepare the lightguide groove. Applicable methods include casting, etching, micro EDM, micro milling, laser cutting, forging, heat extension etc., as long as an open groove extended along the longitudinal direction of the needle body 10, sufficient to accommodate the lightguide 30 is formed in the needle body 10.

The structure of the needle body 10 is preferably designed to accommodate the second section 33 in the lightguide groove 11, when the lightguide 30 is assembled with the needle body 10. The lightguide groove 11 preferably has a fixed inner diameter along its length direction, whereby the narrowing section 32 and the first section 31 will be disposed external to the lightguide groove 11, i.e., beyond the top end of the needle body 10, when the lightguide 30 is assembled with the needle body 10. A tool is used to affix the assembly of the needle body 10 and the lightguide 30 as described above and the assembly is disposed in a mold that provides a cavity having a contour complimentary to the coupling seat 20 and a portion of the needle body 10. Materials for the coupling seat 20 is provided to the cavity to form the coupling seat 20. After the coupling seat 20 is formed, the assembly is removed from the mold, followed by necessary annealing. An optical needle with lightguide groove is formed. In the optical needle so prepared, the first section 31 of the lightguide 30 is aligned with the junction plane of the light source coupling seat 20.

If the coupling seat 20 has a recess 21, the first section 31 of the lightguide 30 is aligned with the recess 21 of the coupling seat 20, such that an end surface of the first section 31 is aligned with the light emitting surface of the light source 40 to be accommodated in the recess 21 of the coupling seat 20.

Figure 4:
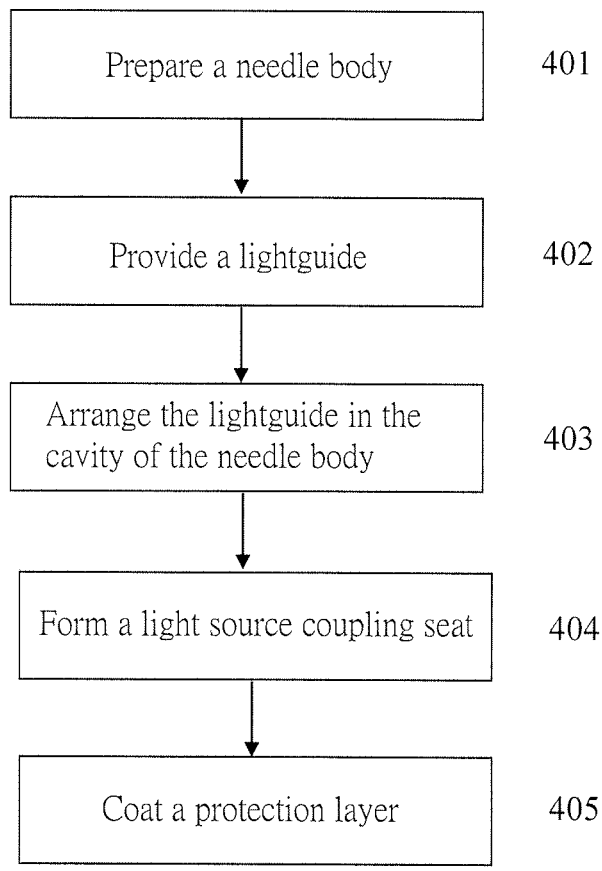
FIG. 4 is the flowchart of the method for preparation of optical needle with lightguide groove in accordance with the present invention.

In the followings, a method for preparation of the optical needle of the present invention will be described. FIG. 4 shows the flowchart of the method for preparation of an optical needle in accordance with the present invention. As shown, in the preparation of the optical needle with lightguide groove of the present invention, firstly at 401 a needle body 10 is prepared. The needle body 10 has a lightguide groove 11 extended along the length direction of the needle body 10. The top end of the needle body 10 may further include a disc extended laterally. Secondly, at step 402 a lightguide 30, in this case an optical fiber, is prepared. The lightguide 30 has a first section 31, a narrowing section 32 connected to the first section 31, and a second section 33 connected to narrowing section 32. The long axis of the lightguide 30 reduces from the junction of the first section 31 and the narrowing section 32 to the junction of the narrowing section 32 and the second section 33. The reduction may be a gradual reduction or a gradient reduction. Then, at 403 the second section 33 of the lightguide 30 is disposed in the cavity 11 of the needle body 10. If the inner diameter of the cavity 11 is fixed, the narrowing section 32 and/or the first section 31 remains outside of the needle body 10. At 404, a light source coupling seat 20 with a junction plane is formed, to encompass a portion of the needle body 100 and the first section 31 and narrowing section 32 of the lightguide 30, while having an end surface of the first section 31 aligned with the junction plane, in order to receive light beams entering through the junction plane. At step 405, a protection layer is coated on the surface of the needle body 10 to cover both the needle body 10 and the lightguide groove 11 and to fill any gap between the needle body 10 and the lightguide groove 11. Preparation of the invented optical needle is thus completed.

In the above embodiment of the present invention, the light source coupling seat 20 does not provide a light recess 21 but, instead, a light source junction plane at the top surface of the coupling seat 20. In such an embodiment, since a narrowing section 32 that is useful in coupling the optical fiber 30 to an optical fiber cable has been provided, simply irradiating the junction plane with a commercially available laser source, such as a laser pointer, would cause the transmission of light power to the second section 33 of the lightguide 30. If the recess 21 is necessary, the recess 21 may be formed at step 404, or in a later step by, such as, milling of laser process. In such a step, the junction plane may also be process to form required optical shape or characters.

In the above steps, the light source coupling seat 20 is preferably formed by molding, such as injection molding. In such examples, the products of step 403 are arranged at suited positions in a mold for the light source coupling seat 20 and maintain their relative positions. A material for the light source coupling seat 20 is filled in the mold to form the coupling seat 20. After necessary annealing and other process, the optical needle with lightguide groove of the present invention is prepared. In order to maintain the relative positions of the lightguide 30 and the needle body 10, certain positioning tools may be used. The tools will become part of the coupling seat 20 after formation of the coupling seat 20.

The optical needle of the present invention may further comprise a light source (not shown). The light source may be an optical cable or a laser head. If the light source is an optical cable, an end of the cable will be connected with a light source (not shown), to generate light power needed in the optical needle, whereby the light power may be transmitted to the optical needle through the cable. In such embodiments, the other end of the optical fiber cable may be inserted in the recess 21 of the coupling seat 20, whereby the narrowing section 32 of the lightguide 30 will couple the light power of the light source to the second section 33 for further use.

In a preferred embodiment of the present invention, the light source is a laser head. The laser head includes a laser beam generator for generating a laser beam. A coupling end may be provided in the laser head, serving as light emitting surfaced plugging end of the laser head. The coupler may be inserted in the recess 21 of the light source coupling seat 20, such that the light emitting surface is aligned with end surface of the first section 31 of the lightguide 30. In this design, the shape and size of the coupling end is preferably compatible with the recess 21, so that the laser head can be inserted and securely positioned in the light source coupling seat 20, whereby the light-emitting surface is aligned with end surface of the first section 31 of the lightguide 30.

Any small-scale laser light generator can be used in the present invention. For example, the commercially available laser pointer that generates red-color laser beams, is applicable in this invention. Since this and other laser sources are well known in the art, details thereof are omitted.

In addition to the types of light source described above, it is also possible to irradiate the junction plane of the coupling seat 20 by a commercially available laser source, such as a laser pointer as described above, to achieve transmission of light powers to the second section 33 of the lightguide 30. In other words, in application an optical fiber cable or a laser head inserted in the coupling seat 20 is not absolutely necessary.

Figure 5:
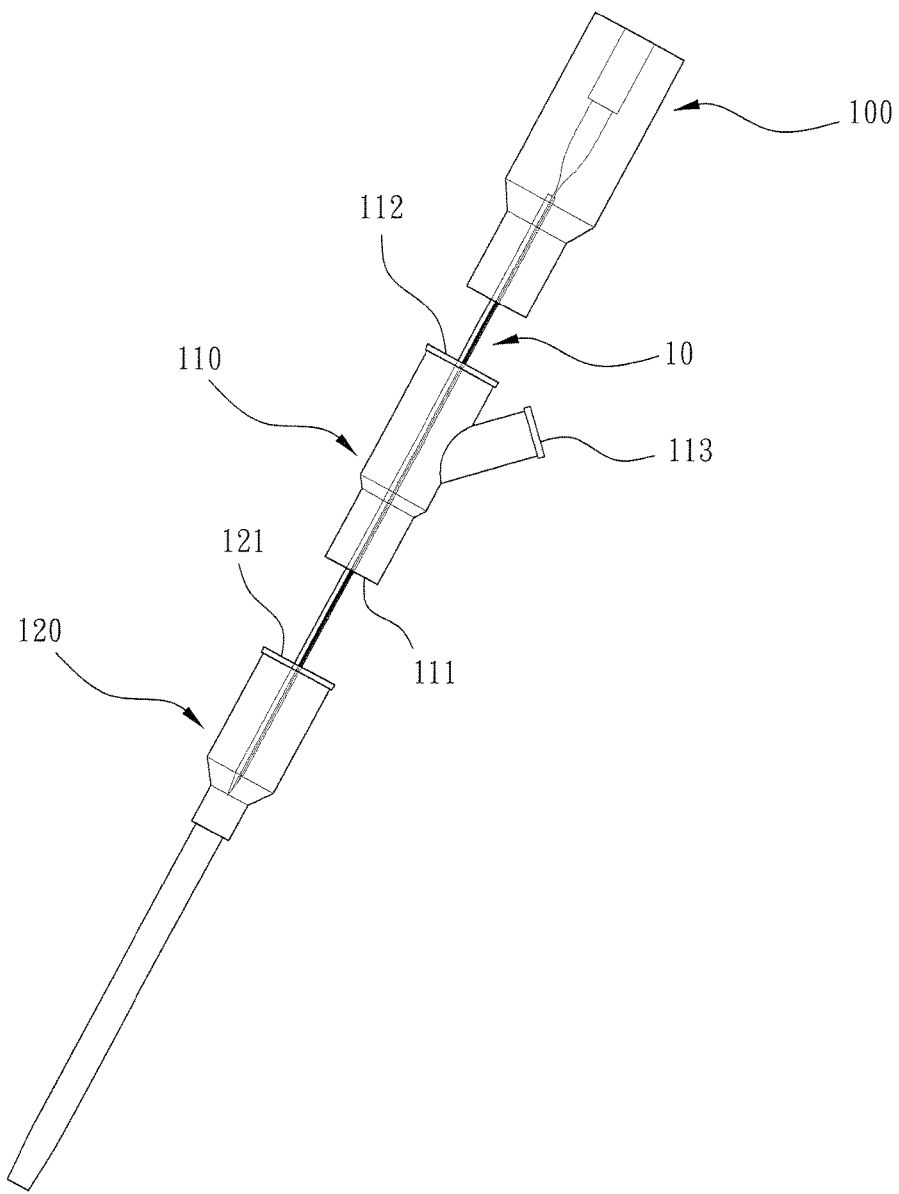
FIG. 5 shows one example of the applications of the invented optical needle.

FIG. 5 shows one example of the applications of the invented optical needle. As shown in the embodiment of this figure, the optical needle with lightguide 100 may be used in a Y-connector 110, to introduce the lightguide 30 into a remaining catheter 120. The remaining catheter 120 may be of any medical, chemical or industrial use. Commonly seen examples of the needle tube include: intraosseous catheter, intravenous catheter, Insertion needle/catheter for hemodialysis arteriovenous fistula, for the purpose of keeping a fluid therapy line in the bone, blood vessels, tissue, abdominal cavity etc. The Y-connector 110 provides an outlet 111 to be inserted into the inlet 121 of the remaining catheter 120. It further provides two inlets 112, 113, in which inlet 112 is for insertion of the optical needle 100 and knelt 113 is for insertion of a fluid tube (not shown), for transportation of liquors, infusion or blood products. In the application example shown in FIG. 5, the optical needle with lightguide groove provides optical powers to end portion of the remaining catheter 120, or to the full length, or beyond the full length, of the remaining catheter 120, to irradiate a target or the surroundings of the remaining catheter 120, such as a human tissue.

As described above, the present invention provides a new structure for the optical needle. The optical needle provides a lightguide groove and is easy to produce and assemble. The lightguide used in this invention is connectable with a variety type of light sources, without the need of an additional coupler. A compact and small-size optical needle that is able to reduce the foot print of the optical needle application system is thus provided.

What is claimed is:

1. An optical needle, comprising a light source coupling seat and a needle body in connection with the light source coupling seat, wherein the needle body provides a lightguide groove extended along a length direction of the needle body so to accommodate a portion of a lightguide; the light source coupling seat provides a junction plane for interfacing a light source and the lightguide; and an end of the lightguide groove is aligned with the junction plane of the light source coupling seat, such that an end of the lightguide to be accommodated in the lightguide groove is aligned with the junction plane; characterized in that a lightguide cavity is formed in the light source coupling seat to accommodate the lightguide, that the lightguide cavity extends from an end adjacent to the junction plane to an end adjacent to the lightguide groove, that a cross-sectional size of the lightguide cavity reduces from the junction plane end to the lightguide groove end, and that the needle body comprises a needle tube and the lightguide groove is provided in the wall of the needle tube.

2. The optical needle according to claim 1, wherein the junction plane is provided in a recess to accommodate a portion of a light source.

3. The optical needle according to claim 1, wherein reduction in cross-sectional size of the lightguide cavity is a gradual reduction.

4. The optical needle according to claim 1, wherein reduction in cross-sectional size of the lightguide cavity is a gradient reduction.

5. The optical needle according to claim 1, wherein a tip of the optical needle forms a diagonal cut.

6. The optical needle according to claim 1, wherein a top surface of the optical needle body laterally extends to form a disc.

7. The optical needle according to claim 1, wherein a top surface of the optical needle body laterally extends to form a funnel-like infundibulum.

8. The optical needle according to claim 1, wherein the light source coupling seat is prepared from a plastic material and encompasses a portion of the needle body and a light source end of the lightguide.

9. An optical needle, comprising a light source coupling seat, a needle body in connection with the light source coupling seat and at least one lightguide, wherein the needle body provides a lightguide groove extended along a length direction of the needle body, so to accommodate a portion of the lightguide; the light source coupling seat provides a junction plane for interfacing a light source and the lightguide; and an end of the lightguide groove is aligned with the junction plane of the light source coupling seat, such that an end of the lightguide away from the lightguide groove is aligned with the junction plane; characterized in that a long axis of the lightguide reduces from a light source end aligned with the junction plane to a lightguide groove end adjacent to the lightguide groove and that the needle body comprises a needle tube and the lightguide groove is provided in the wall of the needle tube.

10. The optical needle according to claim 9, wherein the junction plane is provided in a recess to accommodate a portion of a light source.

11. The optical needle according to claim 9, wherein the light guide is an optical fiber and the long axis is diameter of the optical fiber.

12. The optical needle according to claim 9, wherein reduction in cross-sectional size of the lightguide is a gradual reduction.

13. The optical needle according to claim 9, wherein reduction in cross-sectional size of the lightguide is a gradient reduction.

14. The optical needle according to claim 9, wherein a tip of the optical needle forms a diagonal cut.

15. The optical needle according to claim 9, wherein a top surface of the optical needle extends to form a disc.

16. The optical needle according to claim 9, wherein the light source coupling seat is prepared from a plastic material and encompasses a portion of the needle body and a light source end of the lightguide.

\* \* \* \* \*